(12) United States Patent
Decker et al.

(10) Patent No.: US 8,017,170 B2
(45) Date of Patent: Sep. 13, 2011

(54) UTILIZATION OF EMULSION INTERFACE ENGINEERING TO PRODUCE OXIDATIVELY STABLE LIPID DELIVERY SYSTEMS

(75) Inventors: Eric Andrew Decker, Sunderland, MA (US); David Julian McClements, Northampton, MA (US)

(73) Assignee: University of Massachusetts, Boston, MA (US)

( * ) Notice: Subject to any disclaimer, the term of this patent is extended or adjusted under 35 U.S.C. 154(b) by 445 days.

(21) Appl. No.: 10/651,783

(22) Filed: Aug. 29, 2003

(65) Prior Publication Data

US 2004/0091598 A1 May 13, 2004

Related U.S. Application Data

(60) Provisional application No. 60/406,805, filed on Aug. 29, 2002.

(51) Int. Cl.
*A23D 7/00* (2006.01)
(52) U.S. Cl. .................................... 426/602; 426/542
(58) Field of Classification Search ................ 426/602, 426/542
See application file for complete search history.

(56) References Cited

U.S. PATENT DOCUMENTS

| | | | | |
|---|---|---|---|---|
| 2,197,095 | A | * | 4/1940 | Cuenod ........................ 426/311 |
| 2,282,790 | A | * | 5/1942 | Musher ............................ 554/2 |
| 4,062,882 | A | | 12/1977 | Sen Gupta |
| 4,339,465 | A | | 7/1982 | Strouss |
| 4,501,757 | A | | 2/1985 | Smith et al. |
| 4,533,501 | A | | 8/1985 | Sen Gupta |
| 4,927,657 | A | | 5/1990 | Antaki et al. |
| 5,019,403 | A | | 5/1991 | Krochta |
| 5,576,036 | A | | 11/1996 | Pesheck et al. |
| 2003/0087001 | A1 | * | 5/2003 | Stuchell ........................ 426/41 |
| 2003/0091690 | A1 | * | 5/2003 | Somoto et al. ................. 426/39 |
| 2003/0185960 | A1 | | 10/2003 | Augustin et al. |

FOREIGN PATENT DOCUMENTS

| | | |
|---|---|---|
| CA | 2358321 | 3/2002 |
| EP | 0702902 | 3/1996 |
| JP | 2000104064 | 4/2000 |

OTHER PUBLICATIONS

Demetriades, K. et al. 1997.. Journal of Food Science 62(3)462.*
Tong, L. M. et al. 2000. Journal of Food Science 65(8)1325.*
Demetriades, K et al. 1997. Journal of Food Science 62(2)342.*
Hu, M.; McClements, D.J.; Decker, E.A. Lipid Oxidation in Corn Oil-in-Water Emulsions Stabilized by Casein, Whey Protein Isolate and Soy Protein Isolate. *J. Agric. Food Chem*. 2003, 51:1696-1700.
Hu, M.; McClements, D.J.; Decker, E.A. Impact of Whey Protein Emulsifiers on the Oxidative Stability of Salmon Oil-in-Water Emulsions. *J. Agric. Food Chem*. 2003, 51:1435-1439.
McClements, D.J.; Decker. E.A. Lipid Oxidation in Oil-in-Water Emulsions: Impact of Molecular Environment on Chemical Reactions in Heterogeneous Food System. J. Food Sci. 2000, 65: 1270-1282.
Donnelly, J.L.; Decker, E.A.; McClements, D.J. Iron-Catalyzed Oxidation of Menhaden Oil as Affected by Emulsifiers. J. Food Sci. 1998, 83: 997-1000.
Mei, L; Decker, E.A.; McClements, D.J. Evidence of Iron Association with Emulsion Droplets and its Impact on Lipid Oxidation. Agric. Food Chem. 1998, 46:5072-5077.
Database WPI Week 200029, Thomson Scientific, London, GB; AN 2000-333370 XP00251366.
Database FSTA [Online] Internatioinal Food Information Service (IFIS), Frankfurt-Main, DE; 2005, Losso J N et al: "Random centroid optimization of phosphatidylglycerol stabilized lutein-enriched oil-in-water emulsions at acidic pH." XP002521365 Database accession No. 2005-00-t0832 [document showing the pH range of salad dressings] *abstract*.
Demetriades K et al.: "Physical Properties of Whey Protein Stabilized Emulsions as Related to pH and Naci"; Journal of Food Science, Wiley-Blackwell Publishing, Inc., US, vol. 62, No. 2, Mar. 1, 1997, pp. 342-347, XP000691230, ISSN: 0022-1147 *p. 342; figure 6*.
Tong L M: "Mechanisms of the antioxidant activity of a high molecular weight fraction of whey" J. Agric. Food Chem., vol. 48, 2000, pp. 1473-1478, XP002521363 [published on the web Apr. 14, 2000] *p. 1473, col. 1, lines 1-3* *p. 1477, last paragraph* *abstract*.
Tong L M: "Antioxidant activity of whey in a salmon oil emulsion" Journal of Food Science, vol. 65, No. 8, 2000, pp. 1325-1329, XP002521364 *p. 1325* *abstract* *p. 1329, paragraph Conclusions*.

* cited by examiner

*Primary Examiner* — Carolyn Paden
(74) *Attorney, Agent, or Firm* — Reinhart Boerner Van Deuren S.C (57) ABSTRACT

A method for stabilizing lipid components is provided in which a protein-lipid emulsification product is formed, and the isoelectric point of the emulsification product is determined. The pH of the emulsion is adjusted below the isoelectric point of the protein component in the emulsion system to form an emulsification product having an overall positive net charge. The lipid oxidation rates of these protein-stabilized emulsions are significantly lower at this pH value than of those above the pI of the protein component used in the emulsion system. As the difference between the pH of the emulsion and the pI of the protein component in the emulsion is increased the inhibition of lipid oxidation is also increased. These stabilized emulsification products are particularly useful in the production of water-based foods requiring the addition of inherently unstable oil or lipid components.

6 Claims, 6 Drawing Sheets

UTILIZATION OF EMULSION INTERFACE ENGINEERING TO PRODUCE OXIDATIVELY STABLE LIPID DELIVERY SYSTEMS

This application claims priority benefit from provisional application Ser. No. 60/406,805 filed Aug. 29, 2002, the entirety of which is incorporated herein by reference.

The United States Government has certain rights to this invention pursuant to Grant No. 2001-4526 OGCA# 101A122 from the NRI Competitive Grants Program/USDA.

BACKGROUND OF THE INVENTION

Interest in fortification of foods with nutritionally beneficial lipids is growing. Unfortunately, these applications are limited by the fact that lipids are prone to oxidative deterioration. Indeed, the susceptibility of lipids to oxidation is a major cause of quality deterioration in food emulsions. Such food quality deterioration includes undesirable changes of flavor, texture, shelf-life, appearance and nutritional profile.

Current technologies utilize lipids in bulk form with the lipids being stabilized by exogenous food antioxidants. Nevertheless, these bulk lipids only show moderate oxidative stability. Further, drying and encapsulating lipids has also been used. However, this technology is limited by the high degree of non-lipid materials required and the loss of antioxidant protection once the materials are placed in a water-based food.

Recently, a great deal of research has been focused on oxidation of lipids in oil-in-water emulsions rather than bulk lipids due to the former being more commonly encountered in actual food products. In many studies of oxidation in oil-in-water emulsions, model emulsions have been prepared with synthetic surfactants [e.g. sodium dodecyl sulfate (SDS), dodecyltrimethylaminmonium bromide (DTAB), Brij and Tween] even though not all of these surfactants (e.g. SDS, DTAB, Brij) are approved for food use.

Unlike these synthetic surfactants, proteins represent GRAS food additives that can form physically stable emulsions. For example, the emulsifying properties of whey proteins have been studied for years. The polymerizations of whey proteins in whey protein-stabilized emulsions, the interactions between whey proteins and commonly used surfactants at the emulsion droplet surface, and influence of pH, $CaCl_2$, sucrose, heat treatment and protein concentration on the stability of whey protein stabilized emulsions have been reported.

A better understanding of how proteins can influence oxidative reactions is needed for the development of new antioxidant strategies for oil-in-water emulsions. In particular, environmentally stable systems which can deliver nutritionally beneficial and useful lipids into water-based food, beverage or pharmaceutical products and which are stabilized against oxidation without requiring exogenous antioxidant additives are needed.

SUMMARY OF THE INVENTION

In light of the foregoing, it is an object of the present invention to provide a wide range of protein-stabilized emulsification products designed with improved oxidative stability and/or methods for their production and use, thereby overcoming various deficiencies and shortcomings of the prior art, including those discussed above.

It is an object of the present invention to provide a variety of emulsion systems which maintain oxidative stability once incorporated into water-based foods, beverages or pharmaceutical products, thereby reducing or eliminating the need for exogenous food antioxidants.

It is a related object of the present invention to provide, more particularly, a variety of protein-stabilized lipid systems, which afford multiphase antioxidant protection, and contain small amounts non-lipid materials compared to bulk lipid materials.

It is another object of the present invention to provide a method for preparing a cationic emulsification product that is protein-stabilized against oxidation.

It is another object of the present invention to provide a method for using pH to enhance the oxidative stability of a lipid component in a given protein-lipid emulsification product.

It is yet another object of the present invention to provide a process for lipid fortification of food, beverage or pharmaceutical products using the environmentally and oxidatively stable emulsification products of the present invention, thereby reducing or eliminating the need for exogenous food additives in the end product.

Accordingly, it is an object of the present invention to provide various protein-stabilized oil-in-water emulsions/compositions, thereby overcoming various deficiencies and shortcomings of the prior art, including those outlined above. It will be understood by those skilled in the art that one or more aspects of this invention can meet certain objectives, while one or more other aspects can lead to certain other objectives. Each objective may not apply equally, in all instances, to every aspect of the present invention. As such, these and other objects can be viewed in the alternative with respect to any one aspect of the present invention.

Other objects, features, benefits and advantages of the present invention will be apparent in this summary and descriptions of preferred embodiments, and will be readily apparent to those skilled in the art having the knowledge and experience in the area of food science and engineering. Such objects, features, benefits and advantages will be apparent from the above as taken in conjunction with the accompanying examples, data and all reasonable inferences to be drawn therefrom.

In part, the present invention relates to a method of using a protein to increase the oxidative stability of a lipid in an aqueous medium in which a lipid component/substrate is dispersed in an acidified aqueous phase by a cationic protein-emulsifying component. Preferably, the lipid component includes, but is not limited to: fatty acids, triglycerides and their respective derivatives, carotenoids, terpenes, anti-oxidants, colorants, flavor oils (for example, peppermint, citrus, coconut, or vanilla), nutrients and nutraceuticals or fat soluble vitamins (for example, vitamin E) as may be required by a given food, beverage or pharmaceutical end use application. The present invention, therefore, contemplates a wide range of lipid components including lipids of varying molecular weights containing moieties such as hydrocarbons, alkyls, alcohols, aldehydes, acids, amines, glucides or combinations thereof. It will be readily apparent that, consistent with the broader aspects of the invention, the lipid component can further include other food oils such as corn, soybean, canola, rapeseed, olive, peanut, algal, fish or a combination thereof. In various highly preferred embodiments, the lipid component can include or contain an omega-3 fatty acid or a carotenoid. More generally, such a lipid component can include or contain any poly-unsaturated fatty acid.

The protein component serves to provide environmental and oxidative stability to the emulsification products/compositions of the present invention. The protein emulsifier component allows for dispersibility of the lipid component as dictated by a given end use application and includes proteins that possess a positive net charge at an emulsion pH below the isoelectric point of the protein in the emulsion or system. At this system pH, the protein-emulsifying component is cationic, resulting in emulsion droplets possessing an overall positive net charge. Protein components can be selected on the basis of their amino acid residues (e.g., lysine, arginine, asparatic acid, glutamic acid, etc.) to maximize the overall positive net charge of the protein component, and therefore the cationic character of the emulsion droplets.

Without limitation, the protein component can include any one of the dairy proteins, vegetable proteins, ovalbumins, glycoproteins, mucoproteins, phosphoproteins, serum albumins, collagen and combinations thereof. Collagen, for example, may be particularly useful in the methodology of the present invention given its relatively high isoelectric point, from a pH of about 7.5 to about 8, depending on the particular source and method of hydrolyzation. Thus, the protein-lipid compositions derived therefrom may be used to inhibit oxidation in systems where higher acidities may be deleterious.

In part, the present invention is also directed to a method for preparing a protein-lipid system, wherein the system has dispersed therein a lipid stabilized against oxidation. The method can include (1) providing a lipid component in an aqueous medium limited only by choice of nutritional or physical characteristics desired for an end product, (2) contacting the medium with a protein component and (3) adjusting the pH of the medium to a value less than about the isoelectric point of the protein component in the medium such that the composition has an overall positive charge and/or to provide the protein component positive charge sufficient to effect the physical stability and the antioxidant properties described herein. Alternatively, it will be apparent that pH adjustment can occur before contacting the lipid component with the protein component, such that the pH adjustment of the protein component or lipid component occurs before the emulsification product is formed.

The concentration of the protein component provided need only be an amount sufficient to stabilize the oil-in-water emulsion/compositions of the present invention as dictated by desired dispersion properties. For instance and as illustrated in the examples that follow, the emulsification product can include a protein component and a lipid component of at least about 1 part protein component to about 25 parts lipid component. Alternatively, the present invention can provide compositions containing approximately up to about 30 to about 40 weight percent lipids in aqueous medium and containing very little non-lipid materials compared to bulk lipids of the prior art.

Without limitation to any theory or mode of operation, once the emulsification product is incorporated into an end product, enhanced oxidative stability of the lipid/oil component is exhibited, due in part to the ability of the cationic emulsion droplets to electrostaticly repel prooxidative metal/metallic ions, reducing interaction or contact between the prooxidants and the substrate (e.g. the lipid/oil component). Accordingly, it is observed that as the pH of the emulsion becomes more acidic with respect to the isoelectric point of the protein component, inhibition of oxidation of the lipid/oil component is increased. In the oil-in-water emulsion systems of the present invention, this antioxidant effect is exhibited without the need for added antioxidant materials.

Further, the antioxidant effect of the protein stabilized systems/products of the present invention can also be influenced by (1) the composition of amino acids of the protein component which can serve to inactivate free radicals, (2) the ability of the protein component to form thick viscoelastic films at the emulsion droplet interfaces which physically minimize lipid hydroperoxide-transition metal interactions and/or (3) the ability of the protein component to chelate prooxidant metal ions or quench secondary products of oxidation. Accordingly, the present invention includes design, choice or variation of the protein component depending on the oxidative stability and dispersibility required by the end use application.

In various preferred embodiments, the protein stabilizing component is a dairy protein which includes but is not limited to whey protein isolate (WPI), sweet whey (SW), β-lactoglobulin (β-Lg) or α-lactalbumin (α-La). However, consistent with the broader aspects of this invention, a number of other proteins can be used. For example, oil-in-water emulsions prepared with a vegetable protein (e.g., soy proteins, etc.), ovalbumins, glycoproteins, mucoproteins, phosphoproteins (e.g., casein, vitellin, etc.), serum albumins or similar protein components will exhibit oxidative stability at a pH below the isoelectric point of the protein component. Alternatively, any of the oil or lipid substrates named herein can be first complexed with a carbohydrate component and subsequently emulsified and oxidatively stabilized using the protein components described above. Another variation of the present invention can include use of partially denatured proteins of the kind described herein for emulsification and stabilization of the lipid/oil component.

In part, the present invention is further directed to a method of using pH to enhance the oxidation stability of a protein-lipid composition. The method can include (1) providing an aqueous protein-lipid emulsification product including a protein component and a lipid component and (2) adjusting the pH of the protein-lipid emulsification product to a value that is less than the isoelectric point of the protein in the aqueous protein-lipid emulsification product, whereby the emulsification product has a positive net charge and exhibits increased oxidative stability of the sort described herein. The method can include homogenizing the protein component and the lipid component at a pressure sufficient to form a stable protein-lipid emulsification product.

In part, the present invention is also directed to a method of delivery of nutritionally or physically valuable lipid components that are stabilized against oxidation into water-based end products. Such method includes (1) design and preparation of a protein-stabilized emulsification product as described herein, and (2) incorporation of the emulsification product into the final end product. In particular, this method can be used for fortification of foods, beverages or pharmaceutical products with environmentally and oxidatively stable omega-3 fatty acids, carotenoids, flavor oils, food oils or a combination of these or any of the lipid components described herein.

EXAMPLES OF THE INVENTION

The following non-limiting examples and data illustrate various aspects and features relating to the compositions, complexes and methods of the present invention, including the synthesis of protein-stabilized emulsified lipids which provide multiphase antioxidant protection and use thereof in the synthesis of food products, such compositions as are available through the methodologies described herein. In comparison with the prior art, the present compositions and methods provide results and data which are surprising, unexpected and contrary thereto. It should, of course, be understood that these examples are included for illustrative purpose only and that the invention is not limited to the particular combinations of lipid or protein materials, conditions, properties or the like set forth herein. Comparable utility and advantages can be realized using various other methodologies and/or compositional embodiments consistent with the scope of this invention.

General Methods

WPI, β-Lg and α-La were obtained from Davisco Food International, Inc. and SW was obtained from Kraft Foods. Proteins were used without further purification. The protein content of WPI and SW was 97.6 and 12.1 wt %, respectively. The major protein components of WPI were 55-61% β-lactoglobulin, 19-22% α-lactalbumin, and 6-8% bovine serum albumin. α-Lactalbumin content of α-La powder was 90.6 wt % and β-lactoglobulin content of β-Lg powder 95.0 wt %. All protein concentrations and composition data cited was obtained from the respective manufacturers. Imidazole, sodium acetate, N-ethylmaleimide, ferrous sulfate and cumene hydroperoxide were purchased from Sigma Chemical Co. All other reagents were of analytical grade or purer.

Preparation of salmon oil: Salmon fillets were purchased from a local grocery. The fresh salmon fillets were hand-chopped, minced and centrifuged at 15,000 g for 20 minutes at 5° C. The resulting oil was decanted and stored at −80° C. until use. The salmon oil contained ≧99% triacylglycerols as determined by thin-layer chromatography. Mei, L.; Decker, E. A.; McClements, D. J. Evidence of iron association with emulsion droplets and its impact on lipid oxidation. *J. Agric. Food Chem.* 1998, 46, 5072-5077.

Measurements of Lipid Oxidation

Hydroperoxide Measurements: Emulsions (5 mL) were placed in lightly sealed screw cap test tubes and allowed to oxidize at different temperatures (4.0° C., 20.0° C., and 37.0° C.). Lipid hydroperoxides were measured by mixing 0.3 ml of emulsion with 1.5 ml of isooctane/2-propanol (3:1, v/v) by vortexing (10 sec, 3 times); and isolation of the organic solvent phase by centrifugation at 1,000 g for 2 minutes. The organic solvent phase (200 μL) was added to 2.8 ml of methanol/1-butanol (2:1, v/v), followed by 15 μL of 3.94 M ammonium thiocyanate and 15 μL of ferrous iron solution (prepared by mixing 0.132 M $BaCl_2$ and 0.144 M $FeSO_4$). The absorbance of the solution was measured at 510 nm, 20 minutes after addition of the iron. Hydroperoxide concentrations were determined using a standard curve made from cumene hydroperoxide.

Propanol Measurements: Emulsion samples (1 mL) were placed into 10 mL headspace vials and sealed with poly(tetrafluoroethylene)/butylrubber septa. Headspace propanal was determined using a Shimadzu 17A gas chromatograph equipped with a Hewlett Packard 19395A headspace sampler. The headspace conditions were as follows: sample temperature, 40° C.; sample loop and transfer line temperature, 110° C.; pressurization, 10 s; venting, 10 s; injection, 1.0 minute. The aldehydes were separated isothermally at 70° on a HP methyl silicone (DB-1) fused silica capillary column (50 m, 0.31 mm id., 1.03 μm film thickness). The splitless injector temperature was 180° C., and the eluted compounds were detected with a flame ionization detector at 200° C. Concentrations were determined from peak areas using a standard curve made from authentic propanal.

Statistical Analysis: Assays were measured in triplicate. Statistical analysis was preformed using the student t-test. Snedecor, G. W.; Cochran, G. W. *Statistical Methods*, $8^{th}$ ed.; Iowa State University Press; Ames, Iowa, 1989.

Example 1a

Preparation and Characterization of Emulsions

A 0.2 wt % WPI has been shown suitable for stabilizing 5 wt % oil-in-water emulsions, since emulsions stabilized with this concentration of protein not only produced small droplets with monomodal droplet size distributions, but also had minimal detectable aqueous phase protein. Donnelly, J. L.; Decker, E. A.; McClements, D. J. Iron-catalyzed oxidation of menhaden oil as affected by emulsifiers. *J. Food Sci.* 1998, 63, 997-1000. Without limitation and for the purposes of demonstration, such protein and lipid concentrations were used for the following experiments.

An oil-in-water emulsion was prepared using 5.0 wt % salmon oil, 0.2% protein (WPI, SW, α-La, or β-Lg) and 94.8% 5 mM acetate-imidizole buffer (pH 3.0). In experiments where the role of sulfhydryls in WPI was investigated, WPI was reacted with N-ethylmaleimide (NEM; 3.45 mmol NEM/g protein) for 15 minutes at 25° C. Excess NEM was removed by dialysis of the WPI solution against the 5 mM acetate-imidizole buffer (pH 3.0; WPI solution to buffer 1:100) with 6-8,000 molecular weight cutoff dialysis tubing a total of two times after 6 and 12 hr with constant stirring at 4° C. Oil-in-water emulsions were made by blending the lipid and aqueous phases for 2 minutes using a hand-held homogenizer (M133/1281-0, Biospec Products, Inc.). The coarse emulsion was then homogenized 4 times at 5000 psi through a high-pressure value, two stage APV Lab 1000 homogenizer. The pH of the emulsion was adjusted with 0.1M HCL and/or NaOH after homogenization. The particle size distribution of the emulsions was measured using a Coulter LS 230 laser light scattering instrument. The final emulsion mean particle diameters ranged from 0.73 to 0.80 µm. Droplet size distributions were checked periodically to monitor emulsion stability.

Example 1b

Emulsion droplet charge (zeta potential, $\zeta$) was measured by directly injecting several drops of diluted (1:1,000) oil-in-water emulsions into the measurement chamber of a ZEM5003 Zetamaster (Malvern Instruments). The $\zeta$-potential measurements are reported as the average of two separate injections, with five readings made per injection.

TABLE 1

Zeta potentials of salmon oil-in-water emulsions stabilized by WPI SW, $\alpha$-Lg and $\beta$-Lg at pH 3 and 20.0° C.

| | WPI | SW | $\alpha$-Lg | $\beta$-Lg |
|---|---|---|---|---|
| Zeta potential (mV) | 51.2 ± 1.2 | 33.3 ± 0.6 | 57.8 ± 1.1 | 62.4 ± 0.2 |

Example 1c

Using procedures analogous to those described in the preceding example, the present methods are effected, in accordance with this invention, using emulsions comprising various combinations of the following non-limiting lipid (A) and protein (B) components.

TABLE 2

Emulsion Compositions

| Lipid (A) | Vitamin E and other fat-soluble vitamins, nutrients and nutraceuticals, fatty acids, triglycerides and functional derivatives thereof, carotenoids, terpenes, colorants, flavor oils, food oils (e.g., corn, soybean, canola, rapeseed, olive, peanut) and algal and fishoils |
|---|---|
| Protein (B) | Diary proteins, vegetable proteins (e.g., soy, etc.) ovalbumins, glycoproteins, mucoproteins, phosphoproteins (e.g., casein, vitellin, etc.), serum albumins, collagen |

Such emulsive combinations can be prepared, as would be understood by those skilled in the art—without undue experimentation—as provided herein or using straight forward modifications of known techniques. Likewise, emulsions useful in conjunction with the present methodologies can comprise a range of polypeptides, prepared via known synthetic techniques, designed with incorporation of specific amino acid residues (e.g., lysine, arginine, aspartic acid, glutamic acid, etc) for desired cationic character, isoelectric point and/or end-use application.

Example 2

WPI solubilized in water has a pI of 5.1. Kinsella J E; Whitehead D M. Proteins in whey: chemical, physical, and functional properties. In *Advances in food and nutrition research* Vol. 33; Kinsella, J E, Ed. Academic Press: San Diego, Calif., 1989; pp 343-438. When WPI is absorbed onto the surface of a lipid droplet during the formation of an oil-in-water emulsion, it is possible that the pI would change as the protein conformation changes and the amino acids are exposed to new environments.

Figure 1:
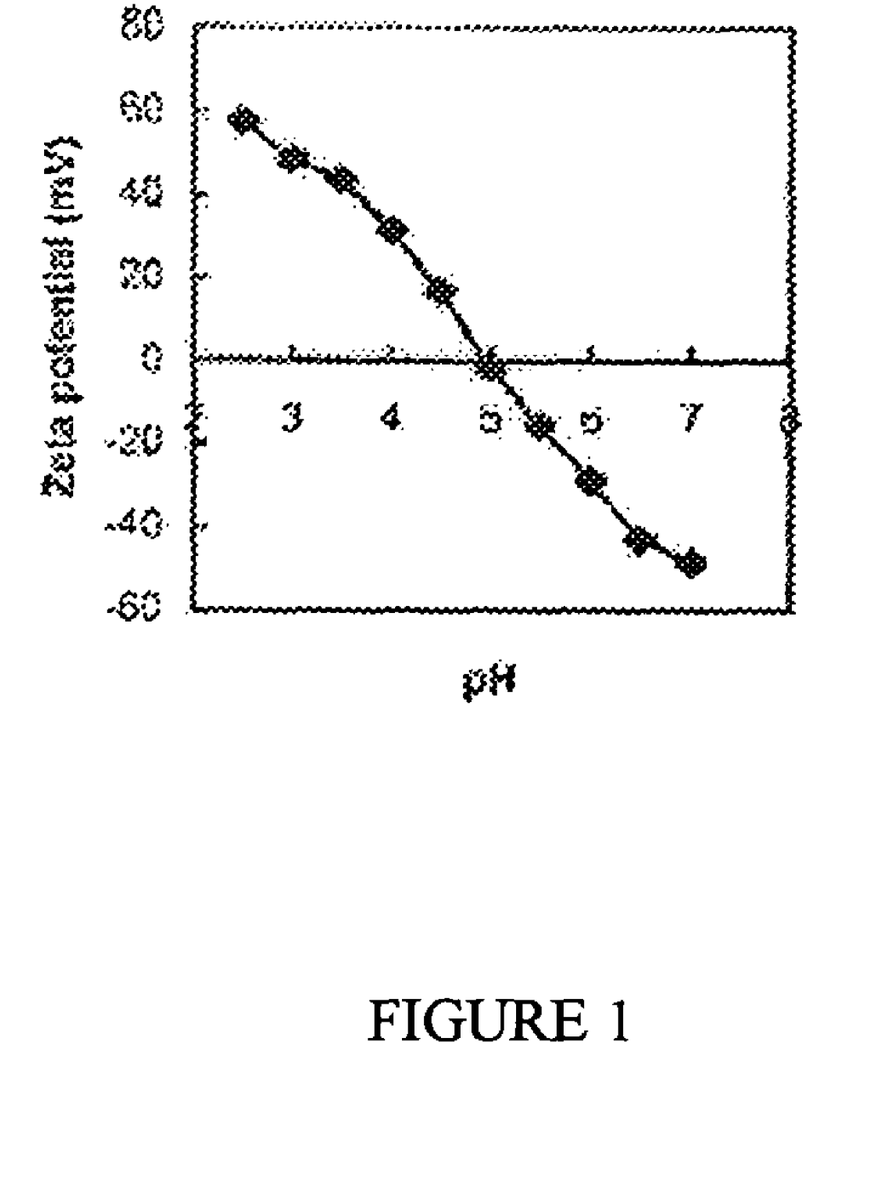
FIG. 1. Influence of pH on the zeta potential of 5% salmon oil-in-water emulsions stabilized by 0.2% whey protein isolate (WPI). Data points represent means (n=5)±standard deviations. Some error bars are within the data points.

In order to determine if the pI of the WPI had been altered by its absorption onto lipid droplets in an oil-in-water emulsion, the electrical charge of the droplets (the zeta potential) was measured as a function of pH. The pI of the WPI on the emulsion droplets was found to be about 4.8 (FIG. 1). This means that at pH's above 4.8 the emulsion droplets stabilized with WPI are negatively charged while at pH<4.8 the droplets are positively charged.

Example 3

Effect of pH on Lipid Oxidation Rates in WPI-Stabilized Oil-in-Water Emulsions.

Figure 2:
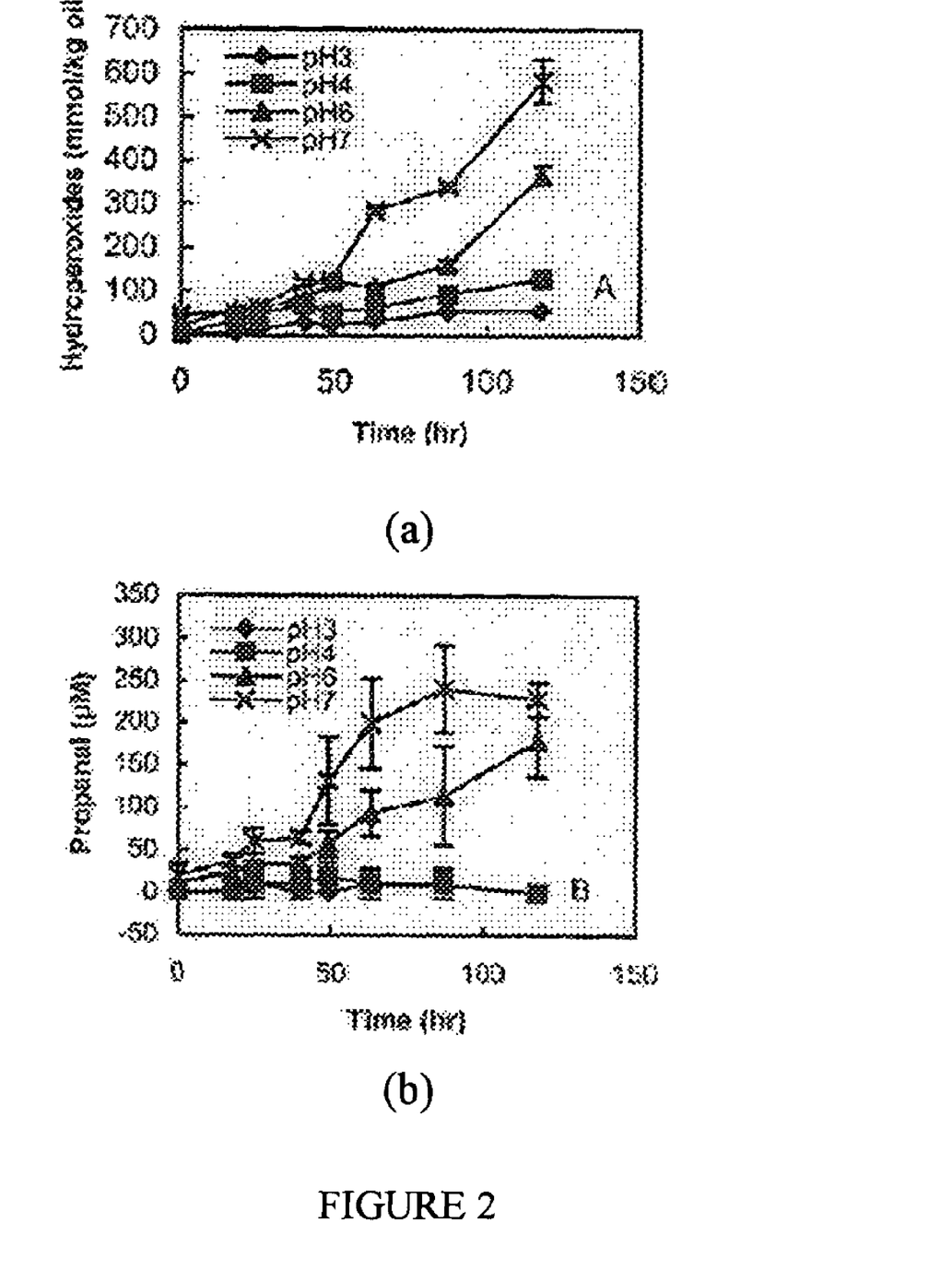
FIG. 2. Influence of pH on the formation of lipid hydroperoxides (a) and headspace propanal (b) in 5% salmon oil-in-water emulsions stabilized by 0.2% whey protein isolate (WPI) at 20° C. Data points represent means (n=3)+standard deviations. Some error bars are within the data points.

FIGS. 2a and 2b illustrate that the formation of lipid hydroperoxides and propanal in WPI-stabilized salmon oil-in-water emulsions increased with increasing pH. Measurements were not made at pH 5.0 since the emulsions were highly unstable to droplet flocculation because the low net charged on the droplet meant that electrostatic repulsion was not sufficient to overcome attractive interactions.

Lipid oxidation rates were significantly lower at pH's below the pI of the WPI. At pH 3.0 and 4.0, lipid hydroperoxide concentrations increased from 2 to 56 and 93 mmol/kg oil, respectively after 87 hr of incubation. This compares to pH 6.0 and 7.0 where initial hydroperoxides concentrations were high (22 and 44 mmol/kg oil, respectively) and hydroperoxides concentrations after 87 hr were 161 and 340 mmol/kg oil, respectively (FIG. 2a).

Propanal formation was also lower at pH's below the pI of WPI with concentrations remaining below 10 µM during the entire incubation period for emulsions at both pH 3.0 and 4.0. This compares to emulsions at high pHs where propanal concentrations were 114 and 240 µM at pH 6.0 and 7.0 after 87 hr of incubation (FIG. 2b). The low oxidation rates at pH values below the pI of the WPI-stabilized emulsion droplets is believed due at least in part to the ability of positively charged emulsion droplets to repel prooxidant iron and thus inhibit oxidation, while negatively charged emulsion droplets attracted iron and accelerated oxidation.

Acceleration of lipid oxidation by anionic emulsion droplets and inhibition by cationic emulsion droplets is in agreement with prior art which reports that negatively charged emulsion droplets stabilized by the synthetic surfactant SDS were able to bind iron and thus accelerate oxidation, while positively charged emulsion droplets stabilized by DTAB did not bind iron and were more oxidatively stable. As the difference between the pH and the pI of the WPI-stabilized emulsion droplet was increased, the inhibition (pH 3.0 compared to pH 4.0) or the acceleration (for pH 7.0 compared to pH 6.0) of lipid oxidation was increased.

Example 4

Effect of Storage Temperature on Lipid Oxidation Rates in WPI-Stabilized Oil-in-Water Emulsions.

Figure 3:
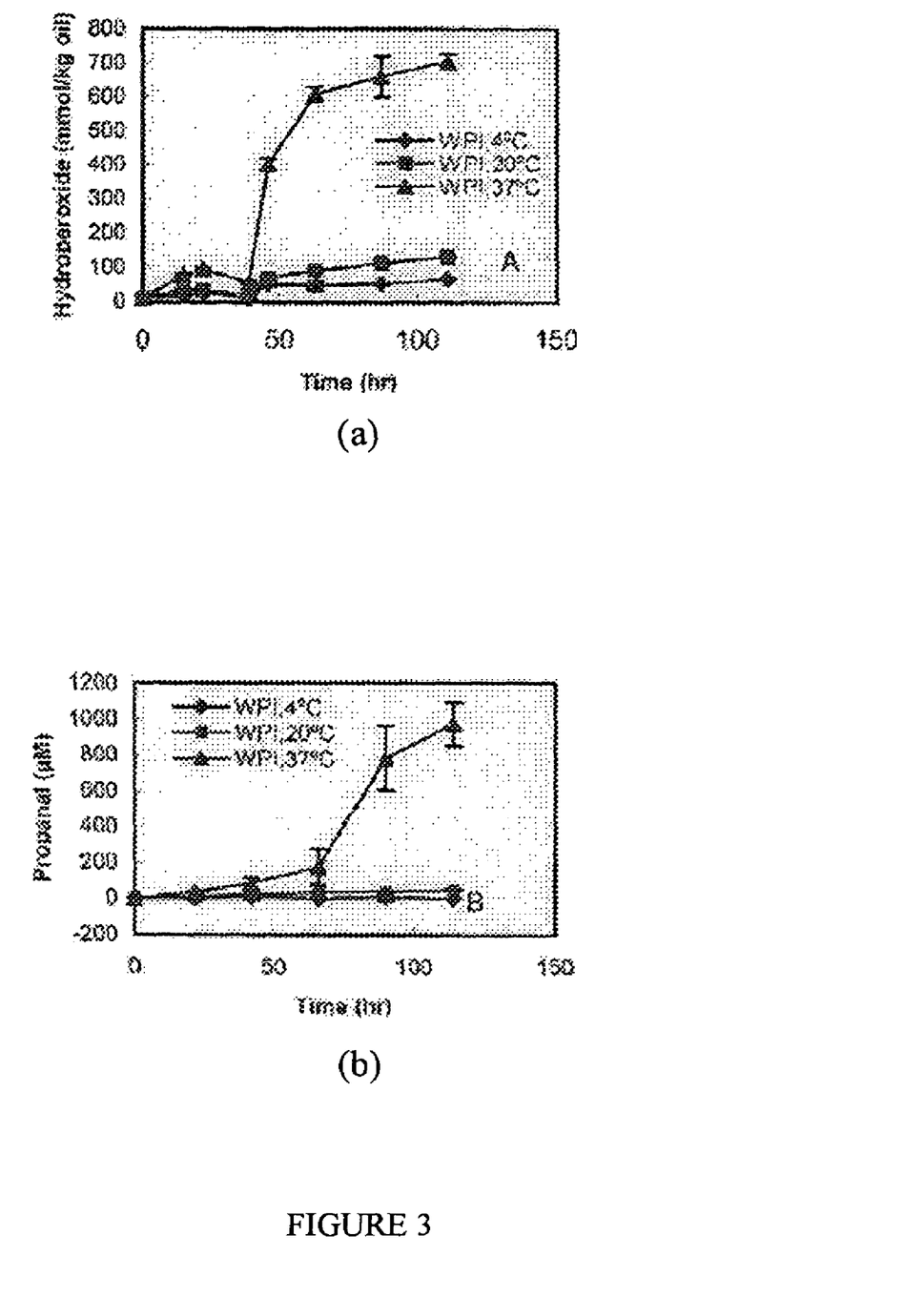
FIG. 3. Influence of temperature on the formation of lipid hydroperoxides (a) and headspace propanal (b) in 5% salmon oil-in-water emulsions stabilized by 0.2% whey protein isolate (WPI). Data points represent means (n=3)±standard deviations. Some error bars are within the data points.
Figure 4:
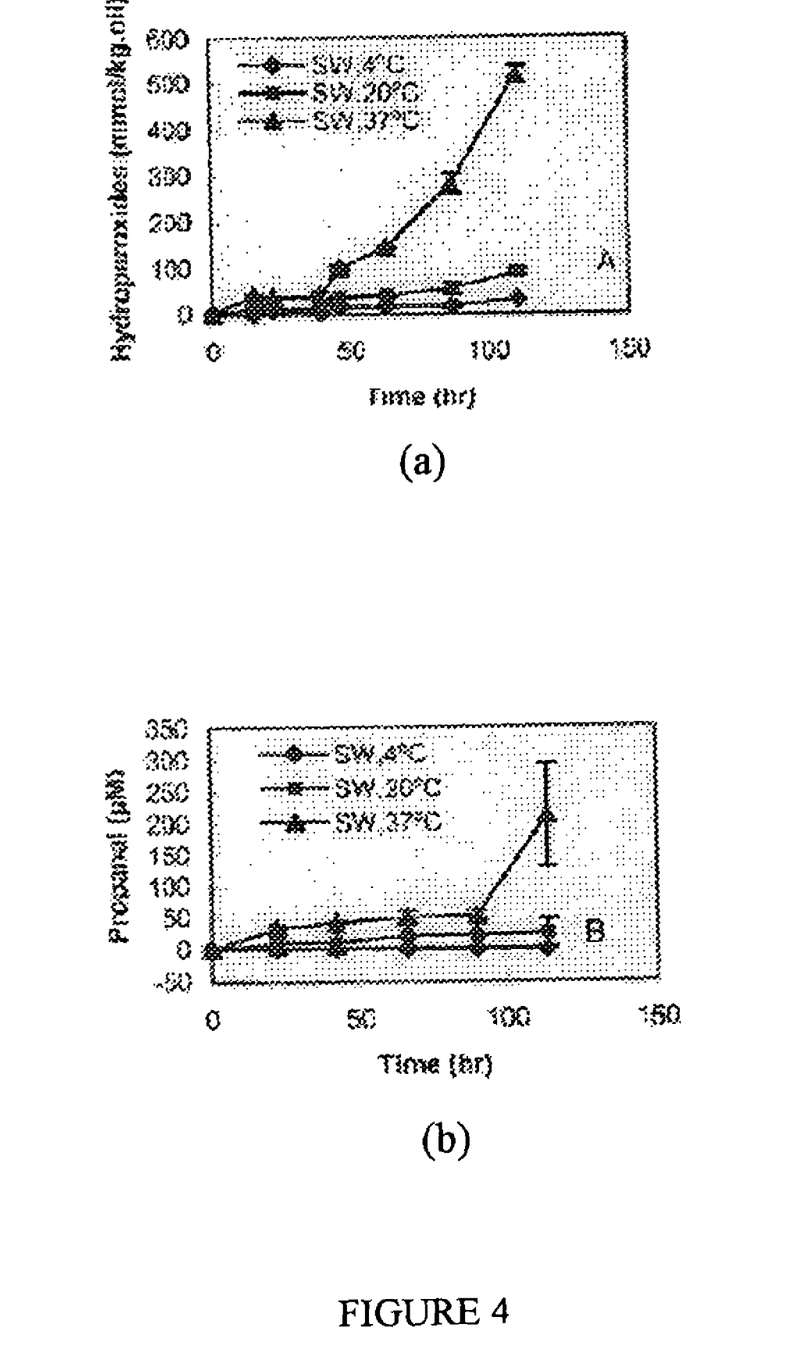
FIG. 4. Influence of temperature on the formation of lipid hydroperoxides (a) and headspace propanal (b) in 5% salmon oil-in-water emulsions stabilized by sweet whey (SW) powder at 0.2% protein. Data points represent means (n=3)±standard deviations. Some error bars are within the data points.

Storage temperature had a significant influence on the oxidative stability of salmon oil-in-water emulsions stabilized with WPI or sweet whey (SW), with increasing storage temperature (4-37° C.) increasing lipid oxidation at pH 3.0 (FIGS. 3a and 3b; 4a and 4b). The effect of temperature on oxidative stability became quite obvious at 37° C. with lipid hydroperoxide concentrations being 5- and 6-fold greater at 37° C. than at 20° C. for WPI and SW, respectively, after 5 days of storage (FIGS. 3a and 4a). Propanal concentrations were approximately 20- and 9-fold greater at 37.0° C. than at 20° C. for WPI and SW respectively after 5 days of storage (FIGS. 3b and 4b).

Example 5

Figure 5:
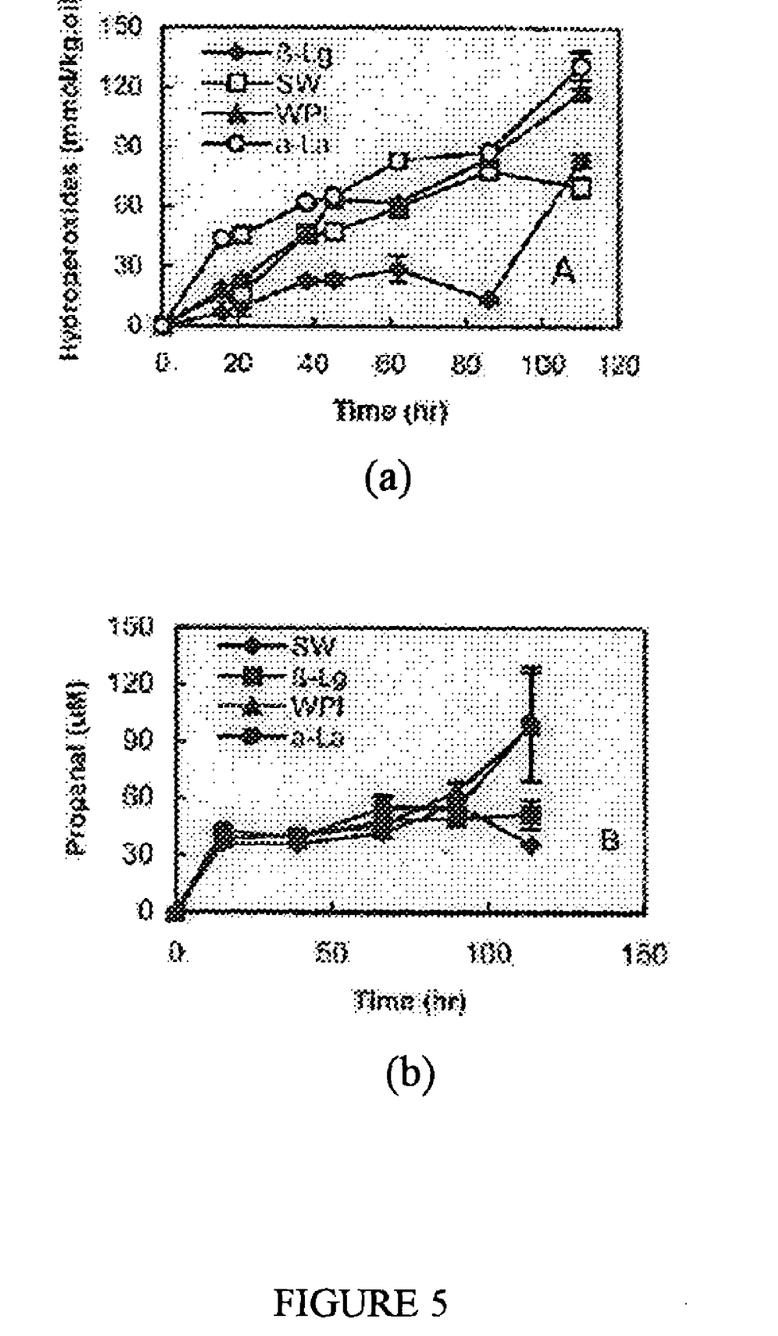
FIG. 5. Formation of lipid hydroperoxides (a) and headspace propanal (b) in 5% salmon oil-in-water emulsions stabilized by 0.2% protein from whey protein isolate (WPI), sweet whey (SW), β-lactoglobulin (β-Lg) or α-lactalbumin (a-La) at 37° C. Data points represent means (n=3)±standard deviations. Some error bars are within the data points.

Comparison of Differences in Oxidative Stability of Emulsions Stabilized by Different Sources of Whey Proteins FIGS. 5a and 5b show the formation of lipid hydroperoxides and headspace propanal in salmon oil-in-water emulsions stabilized with WPI, SW, β-Lg and α-La. All emulsions were prepared with 0.2% protein and 5.0% salmon oil. Oxidation rates increased with increasing pH in emulsions stabilized with all four proteins with strong inhibition of lipid oxidation occurring at pH's (3.0 and 4.0) below the pI's of the proteins (data not shown). Since production of cationic protein-stabilized emulsion droplets is a potential strategy for the production of oxidatively stable emulsions, comparisons between different whey protein-stabilized emulsions were determined at pH 3.0. These emulsions were incubated at 37° C. in order to accelerate oxidation rates thus making it easier to determine differences in the oxidative stability of the samples at pH 3.0.

Oxidative stability was greater for SW- than WPI-stabilized emulsions as determined by the formation of both lipid hydroperoxides and headspace propanal (FIGS. 5a and 5b). SW would contain numerous components not found in the purified WPI such as minerals, citrate, phosphate, lactose and low molecular weight peptides. The greater oxidative stability of the SW-stabilized emulsion is due to the ability of these components to alter oxidation. For example, citrate, phosphate and casein phosphopeptides are known to chelate iron and potentially inhibit lipid oxidation. However, it should be noted that the emulsion made with SW had lower physical stability as evidenced by the formation of a clear serum layer after several days of storage.

Example 6a

To obtain further insights into the ability of interfacially absorbed whey proteins to inhibit lipid oxidation in oil-in-water emulsions at pH 3.0, the effectiveness of commercial whey protein ingredients commonly used in foods (WPI and SW) were compared with that of purified whey proteins (α-La and β-Lg). Samples were stored at 37° C. since oxidation was expected to be slow in the protein-stabilized emulsions at pH 3.0.

β-Lg was found to be the most effective at inhibiting lipid hydroperoxide formation while β-Lg and SW were the most effective at inhibiting headspace propanal formation (FIGS. 4a and 4b). The ability of the whey proteins to alter oxidation rates in protein stabilized emulsions was not solely related to their ability to produce cationic emulsion droplets since the positive charge of the emulsions droplets was in the order of β-Lg>α-La>WPI>SW (Table 1) while inhibition of lipid oxidation was in the order of β-Lg≧SW>WPI≧α-La. This suggests that other factors are also influencing the ability of the absorbed proteins to inhibit lipid oxidation.

Example 6b

Free sulfhydryl groups have been associated with the antioxidant activity of whey proteins due to their ability to scavenge free radicals. This could explain why emulsions stabilized with β-Lg (which has 1 free sulfhydryl) were more oxidatively stable than emulsions stabilized with α-La (no free sulfhydryls).

Figure 6:
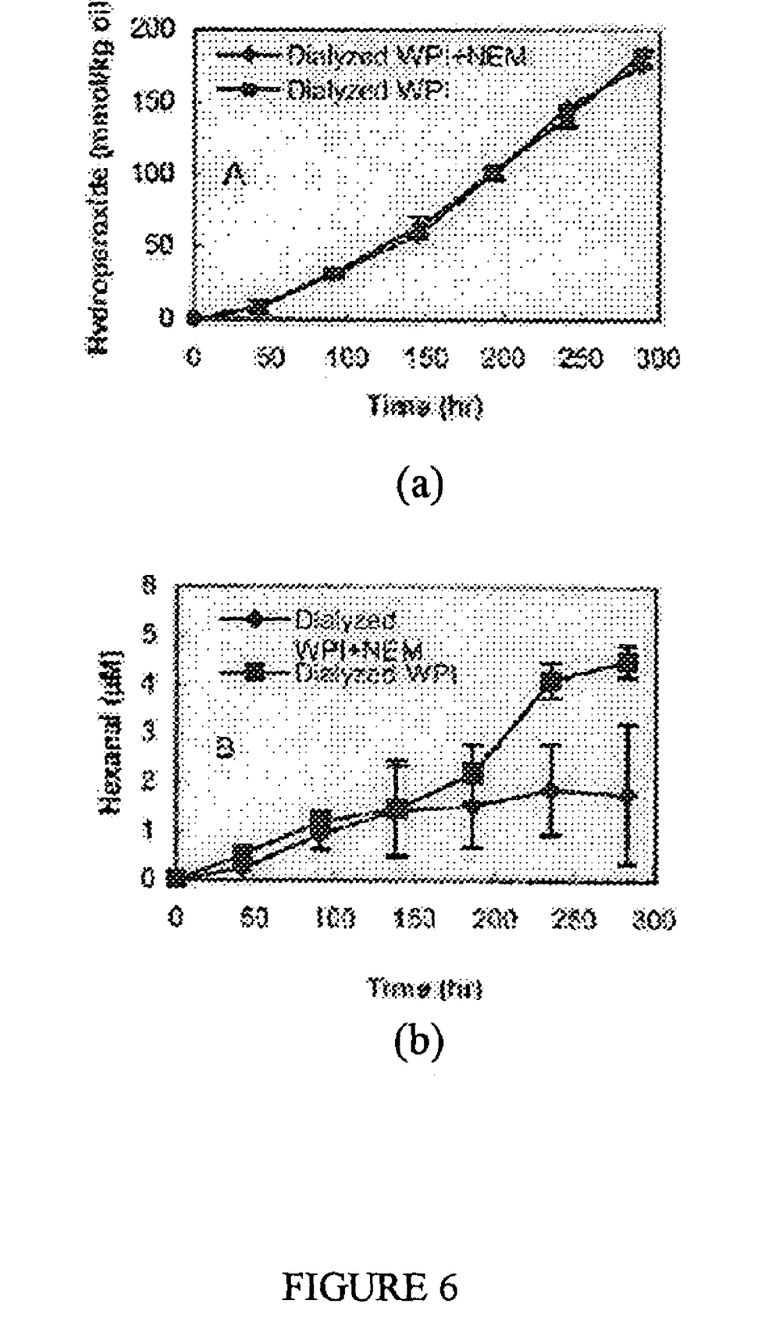
FIG. 6. Influence of N-ethylmaleimide (NEM) on the formation of lipid hydroperoxides (a) and headspace propanal (b) in 5% salmon oil-in-water emulsions stabilized by 0.2% whey protein isolate (WPI). WPI was reacted with NEM and dialyzed prior to formation of the emulsion. Data points represent means (n=3)±standard deviations. Some error bars are within the data points.

To evaluate whether free sulfhydryls in the whey proteins could be involved in inhibition of lipid oxidation in the emulsions, WPI was incubated with NEM to block the sulfhydryls. Corn oil-in-water emulsions were then prepared with WPI and NEM-treated WPI and oxidation rates were compared (FIGS. 6a and 6b). As can be seen, the formation of lipid hydroperoxides was not significantly different for the NEM-treated WPI compared to untreated WPI (FIG. 6a). Formation of headspace hexanol was lower in the presence of NEM (FIG. 6b). If the WPI sulfhydryls were inhibiting oxidation the NEM-treated samples would have been expected to oxidize faster since NEM blocks the antioxidant activity of cysteine. The data of this example suggests that perhaps, without limitation, the free sulfhydryls, at least in the system studied, may have contributed but did not play a major role in oxidation rates.

Whey proteins can also scavenge free radicals through non-sulfhydryl pathways (e.g. tyrosine), a mechanism understood in the art as also influenced by the thermal denaturation of the whey proteins. Therefore, differences in the oxidation rates of the emulsions stabilized by the different whey protein sources may be due, at least in part, to differences in amino acid compositions or differences in exposure of amino acids if the protein sources were heat processed to different degrees. Alternately, the different whey protein sources could produce emulsions with interfacial layers of varying thickness. Previous research has shown that emulsions made with prior art surfactants that produce thick interfacial regions will exhibit slower oxidation rates. Therefore, if the different whey protein sources used herewith produced emulsions with varying interfacial thickness, this may explain the differences in the oxidation rates observed.

Example 7

As described above, the present invention can be used for the incorporation/delivery of oxidatively-stable lipids to a range of food products, beverages or pharmaceutical compositions. Without limitation, with reference to Example 1c, such lipid:protein (A:B) emulsions can be delivered to or incorporated with packaged/canned vegetables, meats and fish, sauces and toppings, condiments, fruit and vegetable juices, carbonated beverages, nutritional drinks/concentrates, dairy or soy beverages, cheeses, yogurts, sauces and spreads.

The invention claimed is:

1. A method of producing a protein stabilized lipid system exhibiting increased oxidative stability comprising:
    providing a lipid component in an aqueous medium;
    contacting the aqueous medium with a protein component to provide the protein component at the interface of the lipid component and the aqueous medium, said protein component selected from whey protein isolate, sweet whey, β-lactoglobulin, α-lactalbumin and combinations thereof;
    adjusting the pH of the aqueous medium to a value less than about the isoelectric point of the protein component, said adjustment sufficient to reduce the rate of oxidation of the lipid component; and
    maintaining the pH of the medium at a value less than about the isoelectric point of the protein component during oxidation of the lipid component, said rate increasingly reduced with increased difference between medium pH and protein component isoelectric point.

2. The method of claim 1 wherein the lipid component is selected from fatty acids, poly-unsaturated fatty acids, triglycerides and functional derivatives thereof, carotenoids, terpenes, anti-oxidants, colorants, flavor oils, food oils, fat soluble vitamins, nutrients, nutraceuticals and combinations thereof.

3. The method of claim 2 wherein the protein component is whey protein isolate and the lipid component comprises an omega-3 fatty acid.

4. The method of claim 1 wherein the stabilized system is introduced to a composition selected from a food product, a beverage, a nutraceutical product and a pharmaceutical product.

5. A method of using pH to enhance the oxidation stability of a protein-lipid composition, comprising:
   providing a protein-lipid emulsification product comprising a protein component selected from β-lactoglobulin, α-lactalbumin and combinations thereof, and a lipid component, said emulsification product without a Tween-20™ surfactant; and
   adjusting the pH of the protein-lipid emulsification product to a value less than about the isoelectric point of the protein component of the protein-lipid emulsification product, whereby the protein component of the protein-lipid emulsification product has a positive net charge;
   maintaining the pH of the emulsification product at a value less than about the isoelectric point of the protein component over days of storage; and
   determining enhancement of oxidative stability by comparing oxidation of the lipid component before and after pH adjustment.

6. The method of claim 5 wherein the emulsification product is introduced to a composition selected from a food product, a beverage, a nutraceutical product and a pharmaceutical product.

* * * * *